(12) United States Patent
Imajo

(10) Patent No.: US 7,292,709 B2
(45) Date of Patent: Nov. 6, 2007

(54) SYSTEM FOR TRANSMITTING PATIENT INFORMATION

(75) Inventor: Kaoru Imajo, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 677 days.

(21) Appl. No.: 10/875,319

(22) Filed: Jun. 25, 2004

(65) Prior Publication Data

US 2004/0263353 A1 Dec. 30, 2004

(30) Foreign Application Priority Data

Jun. 27, 2003 (JP) ............................ P2003-184443

(51) Int. Cl.
*G06K 9/00* (2006.01)

(52) U.S. Cl. ...................... 382/100; 370/324; 370/345; 370/498

(58) Field of Classification Search ................ 382/100, 382/128, 278; 370/324, 345, 464, 498
See application file for complete search history.

(56) References Cited

U.S. PATENT DOCUMENTS 3,854,010 A * 12/1974 Yoshino et al. ............. 348/542
4,596,025 A * 6/1986 Satoh ......................... 375/356
5,517,499 A * 5/1996 Gauffin et al. .............. 370/503
5,535,193 A * 7/1996 Zhang et al. ................ 370/253
6,873,627 B1 * 3/2005 Miller et al. ................ 370/466
6,944,188 B2 * 9/2005 Sinha et al. ................. 370/503
7,123,673 B2 * 10/2006 Czekaj et al. ............... 375/350

FOREIGN PATENT DOCUMENTS

JP          10-192274 A      7/1998
JP         2001-346768 A    12/2001

* cited by examiner

*Primary Examiner*—Vikkram Bali
*Assistant Examiner*—Anand Bhatnagar
(74) *Attorney, Agent, or Firm*—Sughrue Mion, PLLC

(57) ABSTRACT

A plurality of nodes are connected to a network. A first node converts the image signals into image signal data and transmits the same. A second node converts the biological signals into biological signal data and transmits the same. A third node receives the image signal data and the biological signal data. A master counter is provided in one of the nodes to provide a reference count. A first counter in the first node appends a first count to the image signal data. A second counter in the second node appends a second count to the biological signal data. At least one of the first and second counters issues a query to the master counter to receive the reference count as a response. At least one of the first and the second counts is corrected, based on the reference count and a time period from the issuance of the query to the receipt of the response, so as to synchronous with the reference count.

6 Claims, 7 Drawing Sheets

11: image encoder
12: LAN interface
13: counter corrector
14: counter
15: clock source
21: encoder
22: LAN interface
23: count response provider
24: counter
25: clock source
31: LAN interface
32: data reception controller
33: storage
34: display controller
35: input section
36: display section 11: image encoder
12: LAN interface
13: counter corrector
14: counter
15: clock source
21: encoder
22: LAN interface
23: count response provider
24: counter
25: clock source
31: LAN interface
32: data reception controller
33: storage
34: display controller
35: input section
36: display section Fig. 2
start
S1: execute query for count of master counter
store received count and time period required for query communication
S2: 10 times of queries are executed?
S3: calculate count of master counter based on minimum time period
S4: correct count of phantom counter based on calculated count
S5: 50 seconds are elapsed?
Fig. 3
start
S11: query is received?
S12: send count of master counter
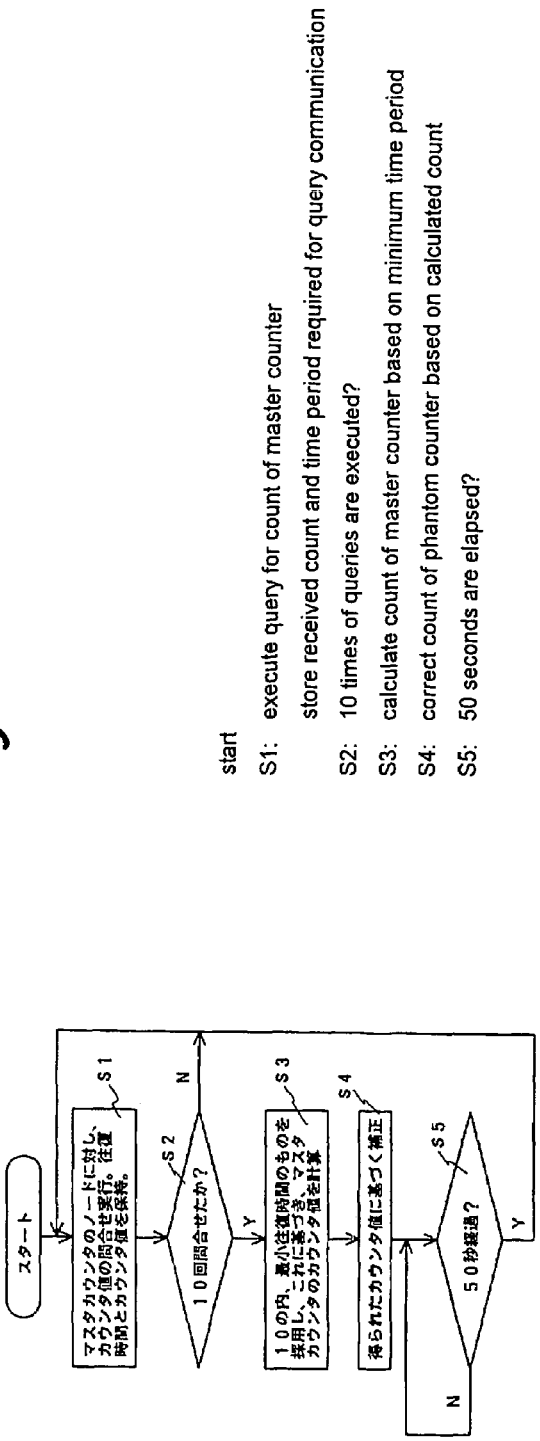
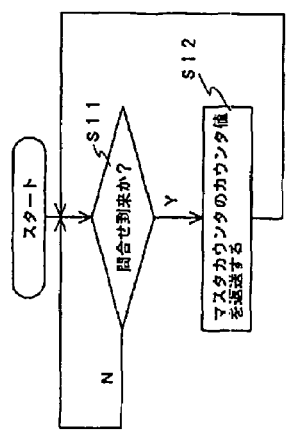

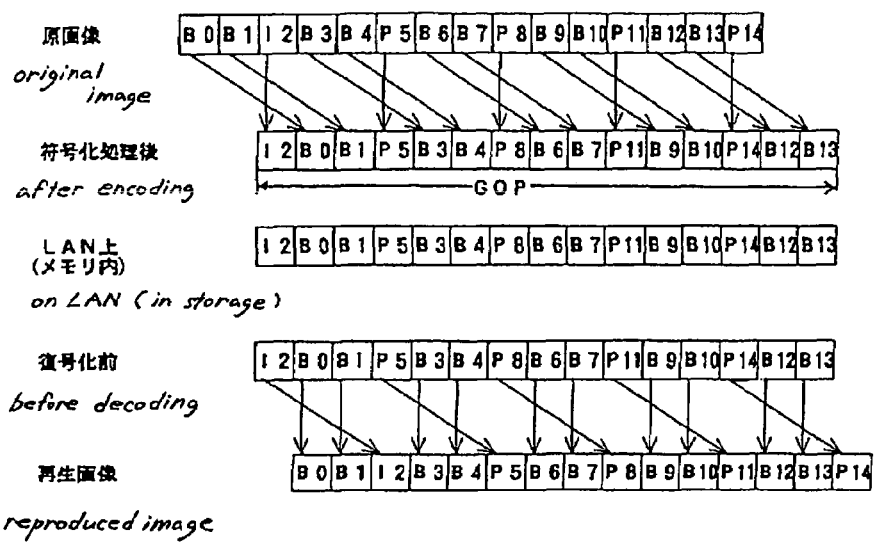

33A: storage area for biological signal data
33B: storage area for image signal data
35: input section
36: display section
341: read-out controller
342: converter/reader
343: parallel/serial converter
345: image memory

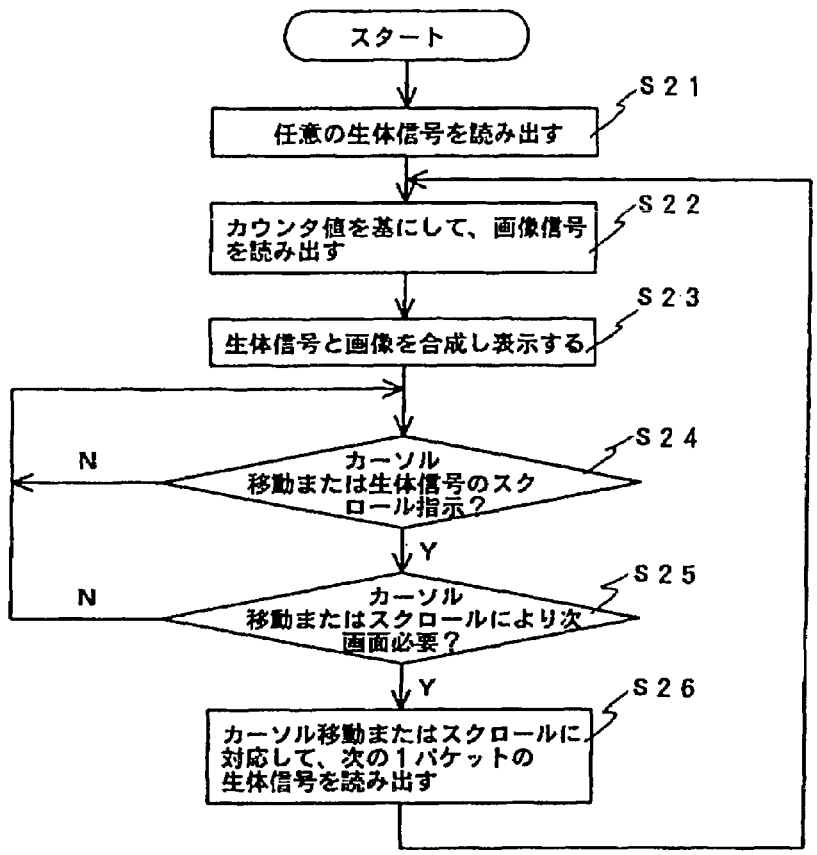

Fig. 8 start

S21: specify arbitrary biological signal
S22: read out image signal data based on count of specified biological signal
S23: display synthesized biological signal and image
S24: command for moving cursor or scrolling biological signal is received?
S25: another screen is required by received command
S26: read out biological signal of another packet in accordance with received command

SYSTEM FOR TRANSMITTING PATIENT INFORMATION

BACKGROUND OF THE INVENTION

The present invention relates to a system for transmitting patient information capable of allowing a receiving side to synchronously reproduce biological signals of a patient such as electroencephalographs and image signals of the same patient.

Japanese Patent Publication No. 2001-346768A discloses a system for performing a remote diagnosis, in which biological signals such as electroencephalographs of a patient and an image signal of the same patient are transmitted via a network and reproduced at the receiving side.

In the above system, a node transmitting a biological signal and a node transmitting an image signal are the same. Accordingly, a common time stamp can be appended onto the biological signal and the image signal, which have been obtained simultaneously, and the signals can be transmitted.

However, when one node is used for transmitting a biological signal and another node is used for transmitting an image signal, the respective nodes differ in clock accuracy. Therefore, in the case where a biological signal and an image signal are transmitted from different nodes and time stamps are appended by the respective nodes, a common stamp may be appended to a biological signal and an image signal which have not actually been obtained simultaneously. Thus, even when a receiving side reproduces such biological signal and image signal having the common time stamp appended thereon, the signals may be actually those which have been obtained at different times.

SUMMARY OF THE INVENTION

It is therefore an object of the invention to provide a system for transmitting patient information capable of allowing a receiving side to synchronously reproduce a biological signal and an image signal which have been transmitted from different nodes. It is also an object of the invention to provide a method of synchronizing these signals.

According to the invention, there is provided a system for transmitting information including image signals and biological signals of a patient via a network, comprising:
  a plurality of nodes connected to the network, including:
    a first node which converts the image signals into image signal data and transmits the image signal data to the network;
    a second node, which converts the biological signals into biological signal data and transmits the biological signal data to the network; and
    a third node, which receives the image signal data and the biological signal data from the network;
  a master counter, provided in one of the nodes to provide a reference count;
  a first counter, provided in the first node to append a first count to a predetermined unit of the image signal data to be transmitted; and
  a second counter, provided in the second node to append a second count to a predetermined unit of the biological signal data to be transmitted, wherein:
    at least one of the first counter and the second counter issues a query to the master counter to receive the reference count as a response; and
    at least one of the first count and the second count is corrected, based on the reference count and a time period from the issuance of the query to the receipt of the response, so as to synchronous with the reference count.

Preferably, one of the first counter and the second counter serves as the master counter. Alternatively, the master counter may be provided in the third node.

Preferably, the third node comprises: a display, adapted to display an image of the patient with biological signal waveforms based on the image signal data and the biological signal data; and a display controller, which synchronizes the image and the biological signal waveforms to be displayed, based on the first count appended to the image signal data and the second count appended to the biological signal data.

With the above configurations, even in a case where the biological signals and the image signal of the patient are transmitted from different nodes, one node can receive these signals which have been securely synchronized, thereby enabling appropriate diagnosis or monitoring of the patient.

According to the invention, there is also provided a method of synchronizing image signals and biological signals of a patient, comprising steps of:
  connecting a plurality of nodes to a network, the nodes including:
    a first node which converts the image signals into image signal data and transmits the image signal data to the network;
    a second node, which converts the biological signals into biological signal data and transmits the biological signal data to the network; and
    a third node, which receives the image signal data and the biological signal data from the network;
  providing a master counter, in one of the nodes to provide a reference count;
  appending a first count to a predetermined unit of the image signal data to be transmitted;
  appending a second count to a predetermined unit of the biological signal data to be transmitted;
  issuing a query from at least one of the first counter and the second counter to receive the reference count as a response; and
  correcting at least one of the first count and the second count, based on the reference count and a time period from the issuance of the query to the receipt of the response, so as to synchronous with the reference count.

Preferably, the method further comprises steps of: providing a display, adapted to display an image of the patient with biological signal waveforms based on the image signal data and the biological signal data; and synchronizing the image and the biological signal waveforms to be displayed, based on the first count appended to the image signal data and the second count appended to the biological signal data.

BRIEF DESCRIPTION OF THE DRAWINGS

The above objects and advantages of the present invention will become more apparent by describing in detail preferred exemplary embodiments thereof with reference to the accompanying drawings, wherein:

FIG. 2 is a flow chart showing operations performed in a counter corrector in the system of FIG. 1;

FIG. 3 is a flow chart showing operations performed in a count response provider in the system of FIG. 1;

FIGS. 5A to 5E are diagrams showing relocation of picture data in a case where the image signal data are subjected to MPEG coding and the thus-encoded MPEG data are subjected to decoding;

FIG. 8 is a flow chart showing a process of synchronous display of the biological signals and an image of a patient performed by the system of FIG. 1.

DETAILED DESCRIPTION OF THE INVENTION

Preferred embodiments of the invention will be described below in detail with reference to the accompanying drawings.

Figure 1:
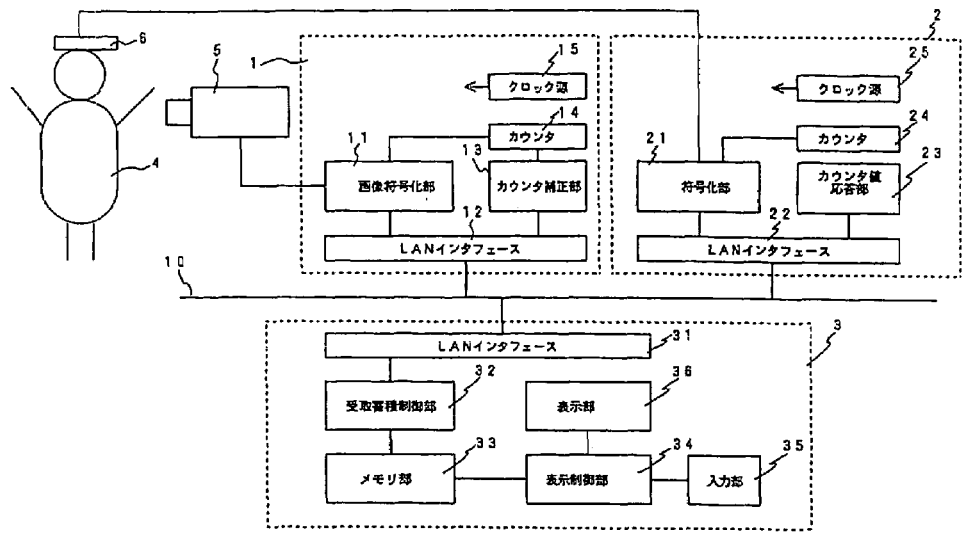
FIG. 1 is a block diagram showing a system for transmitting patient information, according to one embodiment of the invention.

As shown in FIG. 1, a system for transmitting patient information (hereinafter, referred as a patient information transmission system) according to one embodiment comprises a local area network (LAN) 10 to which a first node 1, a second node 2 and a third node 3 are connected.

The first node 1 is a node which transmits image signal data pertaining to a patient 4. Image signals such as NTSC (National Television System Committee) signals obtained from a television camera 5 are sent to the first node 1. The first node 1 is provided with an image encoder 11 for encoding the above image signals into MPEG (Motion Picture Experts Group) data.

In addition to the image encoder 11, the first node 1 is provided with a LAN interface 12, a counter corrector 13, a counter 14, and a clock source 15. The LAN interface 12 communicates data via the LAN 10. The clock source 15 outputs clock signals used by each section of the first node 1. The counter 14 provides a count which is appended to MPEG data by the image encoder 11. The counter corrector 13 is operable to correct the counter 14.

The second node 2 is a node which transmits biological signal data pertaining to the patient 4. Biological signals such as electroencephalographs obtained from a biological signal detector 6 are sent to the second node 2. The second node 2 is provided with an encoder 21 for packetizing and transmitting the biological signals.

In addition to the encoder 21, the second node 2 is provided with a LAN interface 22, a count response provider 23, a counter 24, and a clock source 25. The LAN interface 22 communicates data via the LAN 10. The clock source 25 outputs clock signals used by each section of the second node 2. The counter 24 provides a count which is appended to biological signals by the encoder 21. The count response provider 23 returns a count provided by the counter 24 as a response to a query sent from the counter corrector 13 of the first node 1.

The third node 3 is a node for receiving image signal data sent from the first node 1 and biological signal data sent from the second node 2, and is provided with a LAN interface 31, a data reception controller 32, a storage 33, a display controller 34, an input section 35, and a display section 36. The LAN interface 31 communicates data via the LAN 10.

The data reception controller 32 controls receipt of image signal data and biological signal data via the LAN interface 31 and storage of the received data into the storage 33. The input section 35 is constituted by a keyboard, a mouse, or the like, and is used for inputting control data related to a display. The display controller 34 reads out image signal data and biological signal data from the storage 33 in accordance with control data input from the input section 35. The display section 36 is constituted by a CRT, an LCD, or another display device which displays images and biological signals.

In this embodiment, the counter 24 provided in the second node 2 serves as a master counter. The counter 14 provided in the first node 1 serves as a phantom counter. A phantom counter is a counter which is subordinate to a master counter, and is called a "phantom" (illusion) counter because it does not output a count fully independently. A query for a count is sent from a node where a phantom counter is provided (in this embodiment, the first node 1) to a node where the master counter is provided (in this embodiment, the second node 2). On the basis of the obtained count and a time period required for the query communication (described later in detail), a count of the phantom counter is corrected so as to attain synchronization with the master counter.

The counter 14 counts up in accordance with a clock signal outputted by the clock source 15, and the counter 24 counts up in accordance with a clock signal outputted by the clock source 25. The clock sources 15 and 25 output clock signals having the same frequency; however, the clock sources 15 and 25 have different accuracies or errors. Therefore, after a certain length of time, a discrepancy may be generated between counts of the counter 14 and the counter 24.

The following is an operation for synchronizing (matching) the count of the counter 14 with the count of the counter 24. At initialization, for example, the counter corrector 13 sends a query to the count response provider 23. Here, a count (time stamp) of the counter 24 at the moment the query is sent is referred to as Tm, a count of the counter 14 at the moment when the query is sent is referred to as Ts1, and a count of the counter 14 at the moment when the count Tm is received is referred to as Ts2.

Further, under the assumption that the time period between the issuance of the query from the counter corrector 13 and the receipt of the query at the count response provider 23 and the time period between the issuance of the response from the count response provider 23 and the receipt of the response at the counter corrector 13 are identical, a count of the counter 24 at the moment the counter corrector 13 receives the response is referred as Tm' and represented by the following Equation (1).

$$Tm' = Tm + (Ts2 - Ts1)/2 \qquad (1)$$

However, in the case of transmission of patient information between the first node 1 and the second node 2 over the LAN 10, the time period from the issuance of a query to the receipt of a response (time period required for the query communication; Ts2−Ts1) fluctuates in accordance with the traffic of the LAN 10. For this reason, the counter corrector 13 sends queries for the predetermined times successively, adopts the smallest value among the thus-obtained values (Ts2−Ts1), and determines Tm' using the Tm corresponding to the smallest value of (Ts2−Ts1). In actual cases, in conditions where the LAN 10 had heavy traffic, (Ts2−Ts1) assumed a large value about once every tens of times. Accordingly, in this case, a query is to be performed ten times.

Furthermore, even when synchronization is executed at the initialization, because the clock sources 15 and 25 have different clock accuracies, a discrepancy may be generated between counts of the counter 14 and the counter 24 after a certain length of time. In order to correct the discrepancy, an operation for synchronizing (matching) the count of the counter 14 with the count of the counter 24 is performed at predetermined intervals. The interval depends on a synchronization accuracy required for the system.

In a case where the biological signals are electroencephalographs and the image signals are NTSC signals, a sampling interval of the electroencephalograph signal data which are transmitted from the LAN 10 is approximately 1 msec, and a sampling interval of the image signal data is approximately 30 msec. Here, the system is assumed to be configured so as to ensure synchronization of the image signal data with the electroencephalographs signal data based on the frame accuracy of the image signal data. When a clock accuracy of the counter 24, which is a master counter, is $\gamma 1\%$, a clock accuracy of the counter 14, which is a phantom counter, is $\gamma 2\%$, a time interval for adjusting synchronization is Y, and an accuracy to be secured is v, a clock accuracy achieved by the counter 14 and the counter 24 is $(\gamma 1+\gamma 2)/100$ seconds. That is, it has an error of $(\gamma 1+\gamma 2)/100$ seconds per one second.

The clock accuracy between the counter 14 and the counter 24 during a time interval Y is $Y \cdot [(\gamma 1+\gamma 2)/100]$ seconds. That is, the clock accuracy has an error of $Y \cdot [(\gamma 1+\gamma 2)/100]$ seconds per Y seconds. This accuracy may be equal to an accuracy v to be secured. That is, $v=Y \cdot [(\gamma 1+\gamma 2)/100]$ is established. Accordingly, the following Equation (2) can be obtained.

$$Y=v/[(\gamma 1+\gamma 2)/100] \quad (2)$$

In a case where v=0.03 second, $\gamma 1=0.01\%$, and $\gamma 2=0.02\%$ are applied, Y=100 is obtained from Equation 2. Thereby, it indicates that one correction per 100 seconds is necessary. In an actual case, time interval of correction is set to 50 seconds, because an error fluctuates between positive and negative.

In order to realize the above-mentioned correction, the counter corrector 13 operates as shown in a flow chart in FIG. 2, and the count response provider 23 operates as shown in a flow chart in FIG. 3, which will be described below. At initialization, the counter corrector 13 sends a query for a count to the count response provider 23 in the second node 2 containing therein the counter 24, which is the master counter. The counter corrector 13 holds the time interval from the issuance of a query to the receipt of a response (Ts2=Ts1) and the count Tm obtained at that time (step S1). Upon receipt of the query from the counter corrector 13, the count response provider 23 detects the arrival of the query (step S11) as shown in FIG. 3. When a query arrives, the count response provider 23 retrieves a count of the counter 24 and returns the retrieved count as a response (step S12).

The counter corrector 13 checks if 10 queries have been sent. When completion of 10 successive queries is confirmed, the counter corrector 13 chooses the smallest values of (Ts2=Ts1) among the 10 values of (Ts2=Ts1), each of which is the time interval from the issuance of a query to the receipt of a response. By applying the Tm obtained from the smallest value of (Ts2=Ts1) into Equation 1, the count Tm' of the counter 24, which is the master counter, at the moment of query completion can be obtained. The point when the count Tm' is obtained is later than the point when the smallest value of (Ts2=Ts1) is obtained. This delay is determined, for example, as a discrepancy between the current count Tn and the count Tm'. The counter 14 is corrected by adding the thus-obtained value to the count Tm' in Equation 1 (step S4). The counter corrector 13 uses an output of the counter 14 or that of the clock source 15, and waits until 50 seconds elapses (step S5). After 50 seconds, the steps are repeated from step S1.

As described above, the value of the counter 14 can be synchronized (matched) with the value of the counter 24. The counters 14 and 24 are assumed to count up every predetermined milliseconds. Electroencephalographs (biological signals) obtained at the biological signal detector 6 are subjected to A/D conversion at the biological signal detector 6, then transmitted to the encoder 21 by serial transmission. The encoder 21 performs parallel conversion of the serial digital electroencephalograph signals, and sends them as a packet, which is composed of a predetermined amount of data, via the LAN interface 22.

Figure 4A:
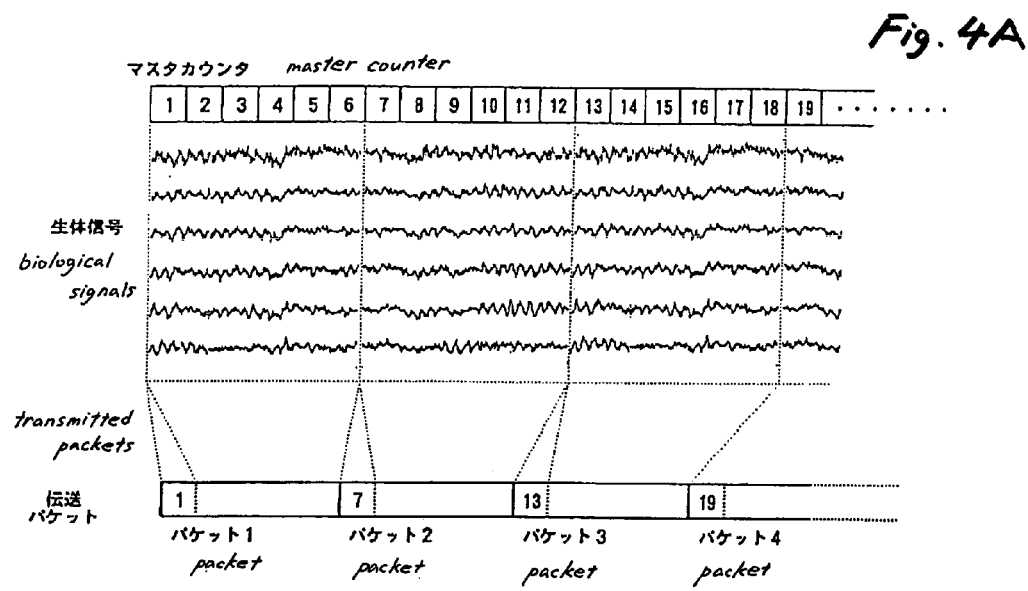
FIG. 4A is a diagram illustrating the manner in which the system of FIG. 1 appends counts into biological signal data.

In regard to the above packetization, the encoder 21 gains a count from the counter 24, and appends the corresponding count to each packet as a time stamp. Here, a sampling rate of the A/D conversion at the biological signal detector 6 is 100 to 200 Hz, and data corresponding to sampling points 100 to 200 are included in 1 sec. FIG. 4A shows that a predetermined volume of electroencephalograph signal data is contained in one packet, and a count of the counter 24 is appended to each packet as a time stamp. An example in FIG. 4A shows that counts of "1," "7," "13," "19" . . . are appended in a predetermined area of packets having packet numbers 1, 2, 3, 4, . . . respectively.

Figure 4B:
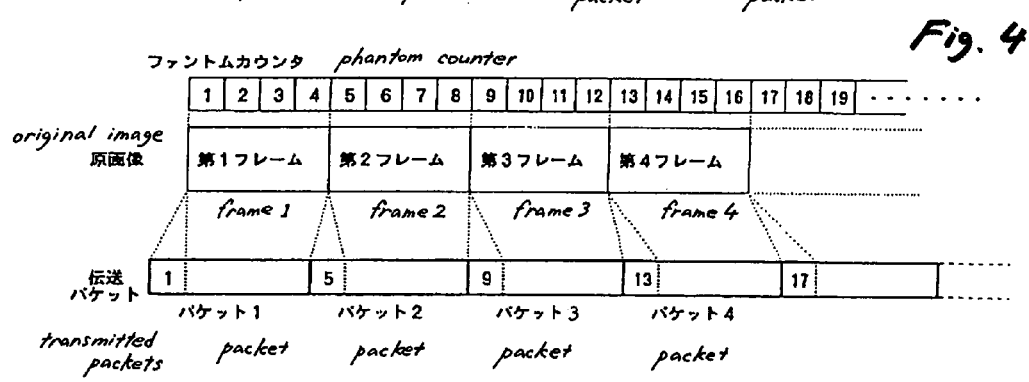
FIG. 4B is a diagram illustrating the manner in which the system of FIG. 1 appends counts into image signal data.

Meanwhile, an image signal of the patient 4 (e.g., an NTSC signal) obtained with the television camera 5 is sent to the image encoder 11, where it is processed into MPEG data. At this moment, the image encoder 11 acquires a count from the counter 14 per each picture, and appends the count thereon as a time stamp. As shown in FIG. 4B, each of counts for the packets having packet numbers 1, 2, 3, . . . , "1," "5," "9" . . . is appended to a predetermined area of each packet. In the example illustrated in FIG. 4B, the original image data are packetized into an MPEG data packet while the sequence of images remains unchanged. However, in actually, as shown in FIGS. 5A and 5B, "B" pictures of the original image are relocated within one group of pictures (GOP) in the process of encoding one GOP into MPEG data. Therefore, on the LAN 10, counts of packets are not transmitted while being aligned in a simple order of count as shown in FIG. 4B.

The biological signal data on which the count is appended as described above are transmitted from the second node 2 to the third node 3. In the third node 3, the data reception controller 32 receives the biological signal data via the LAN interface 31, and then stores the received data in the storage 33. Similarly, the MPEG data (image signal data) on which the count is appended are transmitted from the first node 1 to the third node 3, and are stored in the storage 33. At the moment of the above step, a sequence of the pictures within the storage 33 is the same as that on the LAN 10 as shown in FIG. 5C.

Figure 6:
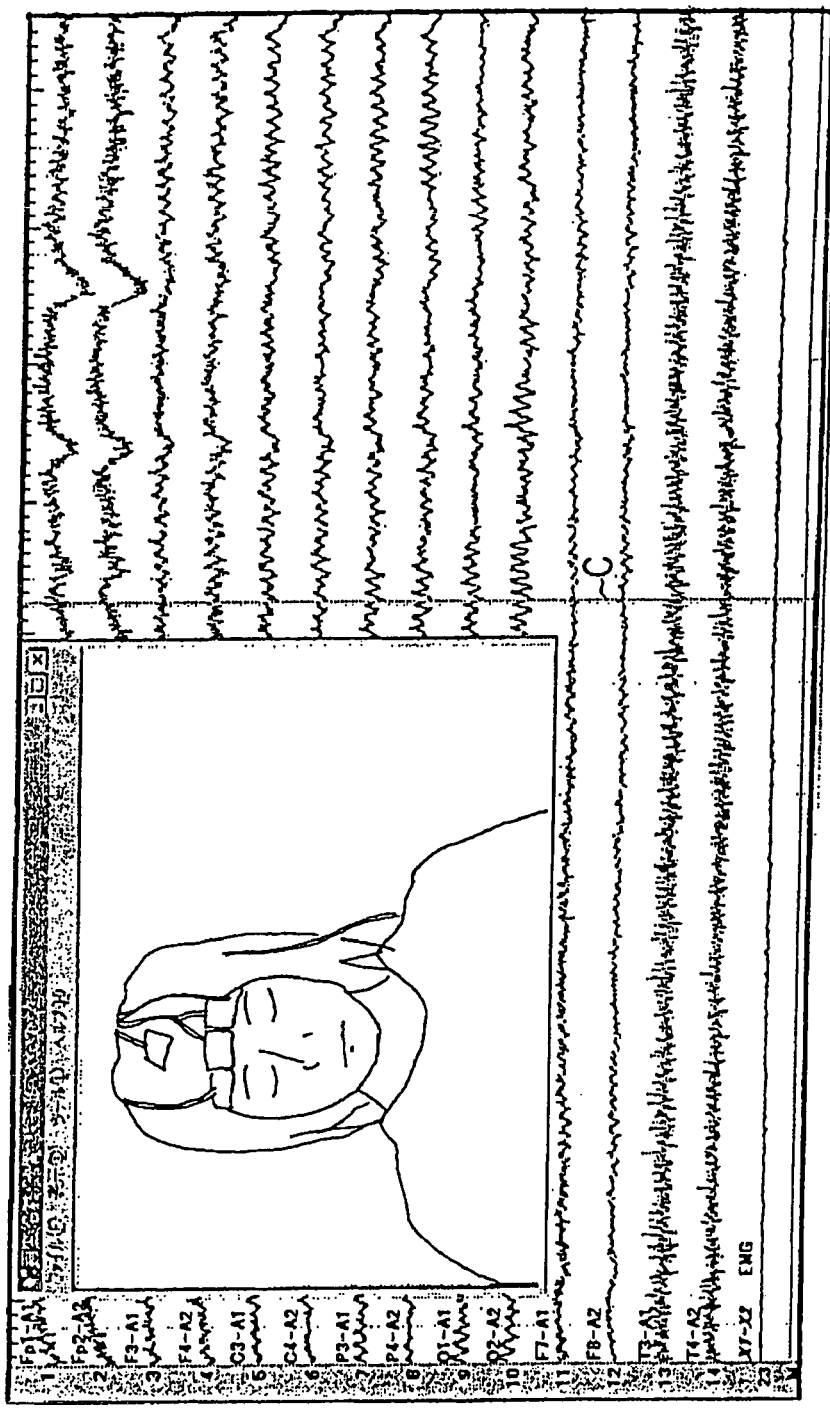
FIG. 6 shows an example display wherein biological signals and an image are displayed in synchronization.
Figure 7:
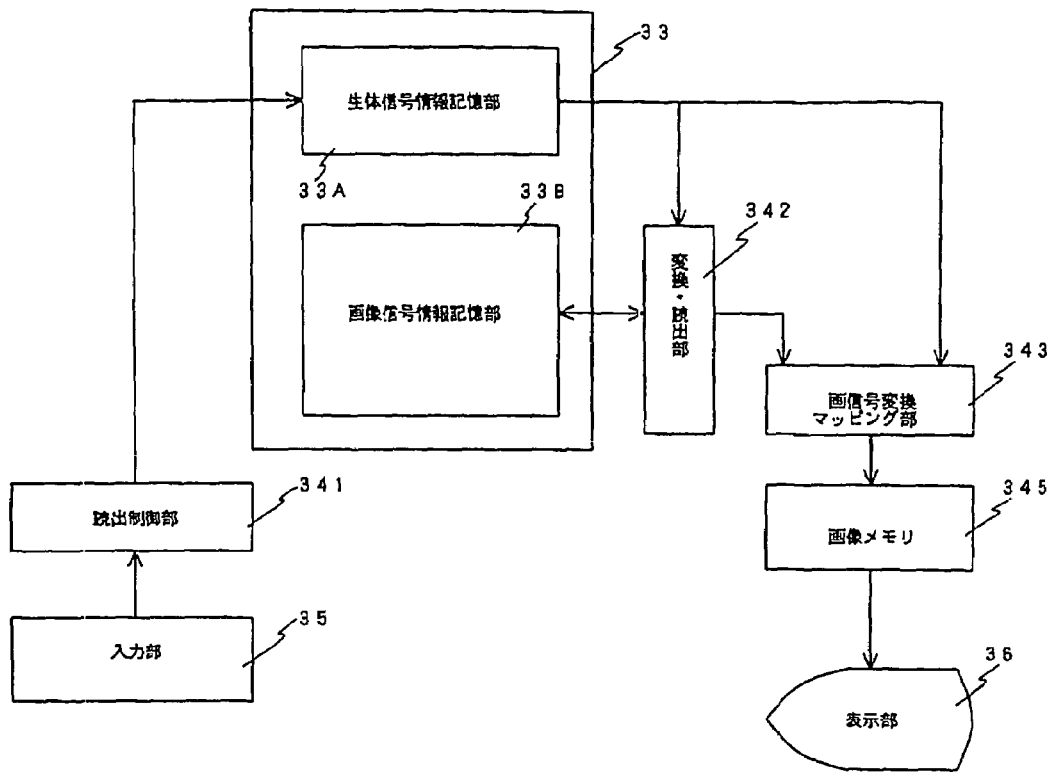
FIG. 7 is a block diagram showing the detail of a display controller in the system of FIG. 1.

When the display controller 34 receives control data from the input section 35, the display controller 34 reads out the biological signal data and the image signal data, both being stored in the storage 33, and displays them on a single screen of the display section 36 as shown in FIG. 6. In this step, the display controller 34 synchronizes the displayed image and the biological signal wave forms. FIG. 7 shows a detailed configuration for achieving the synchronization.

The storage 33 includes a storage area 33A in which biological signal data are stored, and a storage area 33B in which image signal data are stored, and the biological signal data are read out by a read-out controller 341. The read-out biological signal data are delivered to a converter/reader 342 and to a parallel/serial converter 343. The converter/reader 342 retrieves a count from the read-out biological signal data (1 packet), converts the count into a read-out control information for obtaining a corresponding image signal data (1 picture), and reads out image signal data (1 picture) by use of the read-out control information.

More specifically, the converter/reader 342 specifies and reads out 1 GOP of MPEG data including image signal data (1 picture) corresponding to the count retrieved from the biological signal data, and thereupon reproduces plural sets of frame data. Then, among the plural sets of frame data, the converter/reader 342 retrieves one set of frame data and outputs image signal data corresponding to the count retrieved from the biological signal data.

The biological signal data read out from the storage area 33A is delivered to the parallel/serial converter 343, where the biological signal data are parallel/serial converted into data which can be displayed on the screen of the display section 36, and then stored in an image memory 345. Meanwhile, the image signal data, which have been read out from the storage area 33B by the converter/reader 342 and decoded from the MPEG data into reproduced data of the original image, are delivered to the parallel/serial converter 343, where the image signal data are written in the image memory 345 in accordance with the area to be displayed.

Biological signal and image data to be displayed on the screen can be changed from the input section 35 by: inputting commands for displaying biological signals and image data and inputting a count; operating cursor keys to move a cursor C (FIG. 6) of an image displayed on the display section 36; or operating scroll keys to cause a screen scroll. Operations performed in such cases will be described by use of a flow chart shown in FIG. 8.

A display starts when, from the input section 35, a command to display biological signal and image data is inputted and a specific count is inputted. Upon receipt of the above, the read-out controller 341 outputs an address corresponding to the count to the storage area 33A.

For example, it is assumed here that each packet of the biological signal data is stored in a corresponding one of the sequential addresses in the storage area 33A. Also, it is assumed that the sequential packets have counts which are stepped up from 1 in intervals of "6" counts. When a command to read-out the biological signal data having a count "7" is inputted, the count "7" corresponds to the second packet shown in FIG. 4A. In order to read out the second packet, a second address is outputted. In other words, a corresponding address is determined by searching for a packet which includes the specific count. Through these steps, an arbitrary biological signal data specified by the input section 35 can be read out from the storage area 33A (step S21).

A count "7" is appended to the biological signal data. The converter/reader 342 retrieves the count "7" and uses it to read out the image signal data corresponding to the count "7." The converter/reader 342 has a conversion program for converting a GOP corresponding to the count retrieved from biological signal data, and uses the program to read out the corresponding GOP among sets of GOP stored in the storage area 33B.

Here, it is assumed that MPEG data are stored in the storage area 33B at per one address from the first address in numerical order and in units section of one GOP. When one GOP is assumed to correspond to 0.5 second, and a count to "300," the count steps by "300" as the address steps one. Consequently, because the count "7" corresponds to an image of GOP stored in the first address, the GOP data stored in the first address are read out by the converter/reader 342 to reproduce the data of the original image (FIGS. 5D and 5E).

In this step, because counts, as well as the sequence of the original images, are appended to the reproduced images, the frame data of the count "5" (a second frame in FIG. 4B) which includes the count "7," is retrieved and the image to which the count "7" is appended is outputted. In other words, a corresponding image is outputted by searching for frame data which includes the count which has been appended to the biological signal data. When operations of the step S22 are completed as described above, the biological signal data and the image signal data are synchronized and stored in the image memory 345 to display a synchronized image (step S23).

FIG. 6 shows an example of a synchronized image. Electroencephalograph waveforms, which are biological signal waveforms, can be moved by operating a cursor key (or a scroll key) of the input section 35. As shown in a flow chart in FIG. 8, the read-out controller 341 detects whether a command to move the cursor C has been entered by a cursor key or whether a command to scroll has been entered by a scroll key (step S24), and if the command has been entered, the read-out controller 341 detects whether the cursor movement or the scroll requires another screen (step S25). Specifically, when a command to move the cursor C or a command to scroll is continued until the movement or the scroll exceeds the amount of one packet of biological signal, processing branches to YES, and reads the next packet of biological signal data (step S26), then, proceeds to step S22. In step S22, the converter/reader 342 retrieves the count appended to the biological signal data, and reads out the image signal data corresponding to the count. Further, operations after step S22 are processed in the same manner as the example described above.

As described above, according to the embodiment, even when electroencephalograph signal data of the patient 4 are transmitted from the second node 2 and image signal data which include motion picture of the patient 4 are transmitted from the first node 1, because the data include appropriate counts for synchronizing and reproducing the electroencephalograph signal data and the image signal data, accurate reproduction and display on a single screen can be achieved at the third node 3.

In this embodiment, the first node 1 is provided with the phantom counter, and the second node 2 is provided with the master counter. However, the second node 2 may be provided with the phantom counter and the counter corrector 13, and the first node 1 may be provided with the master counter and the count response provider 23. In addition, each of the first node 1 and the second node 2 may be provided with the phantom counter and the counter corrector 13, and the third node 3 may be provided with the master counter and the count response provider 23.

Furthermore, there may be configured that another node which is not shown in FIG. 1 is provided with the master counter and the counter response provider 23, and each of the first node 1 and the second node 2 may be provided with the phantom counter and the counter corrector 13.

In the above description, electroencephalographs are explained as an example of biological signal. However, the invention can be applied to other biological signals, including electrocardiogram signals or electromyogram signals. In such cases, respective biological signals are delivered to independent nodes, and counts provided to the plurality of nodes and a count provided to a node which transmits image signals are to be synchronized.

Arbitrary combinations of a node which is provided with the master counter and the count response provider 23 and a node which is provided with the phantom counter and the counter corrector 13 can be selected. In addition, image signal data referred to in the invention are not limited to those obtained by capturing an outlook image of the patient 4. The invention can also be applied to image signal data obtained by ultrasonic waves or the like.

What is claimed is:

1. A system for transmitting information including image signals and biological signals of a patient via a network, the system comprising:
    a plurality of nodes connected to the network, including:
        a first node which converts the image signals into image signal data and transmits the image signal data to the network;
        a second node, which converts the biological signals into biological signal data and transmits the biological signal data to the network; and
        a third node, which receives the image signal data and the biological signal data from the network;
    a master counter, provided in one of the nodes to provide a reference count;
    a first counter, provided in the first node to append a first count to a predetermined unit of the image signal data to be transmitted; and
    a second counter, provided in the second node to append a second count to a predetermined unit of the biological signal data to be transmitted, wherein:
    at least one of the first counter and the second counter issues a query to the master counter to receive the reference count as a response; and
    at least one of the first count and the second count is corrected, based on the reference count and a time period from the issuance of the query to the receipt of the response, so as to synchronous with the reference count.

2. The system as set forth in claim 1, wherein one of the first counter and the second counter serves as the master counter.

3. The system as set forth in claim 1, wherein the master counter is provided in the third node.

4. The system as set forth in claim 1, wherein the third node comprises:
    a display, adapted to display an image of the patient with biological signal waveforms based on the image signal data and the biological signal data; and
    a display controller, which synchronizes the image and the biological signal waveforms to be displayed, based on the first count appended to the image signal data and the second count appended to the biological signal data.

5. A method of synchronizing image signals and biological signals of a patient, comprising steps of:
    connecting a plurality of nodes to a network, the nodes including:
        a first node which converts the image signals into image signal data and transmits the image signal data to the network;
        a second node, which converts the biological signals into biological signal data and transmits the biological signal data to the network; and
        a third node, which receives the image signal data and the biological signal data from the network;
    providing a master counter, in one of the nodes to provide a reference count;
    appending a first count to a predetermined unit of the image signal data to be transmitted;
    appending a second count to a predetermined unit of the biological signal data to be transmitted;
    issuing a query from at least one of the first counter and the second counter to receive the reference count as a response; and
    correcting at least one of the first count and the second count, based on the reference count and a time period from the issuance of the query to the receipt of the response, so as to synchronous with the reference count.

6. The method as set forth in claim 5, further comprising steps of:
    providing a display, adapted to display an image of the patient with biological signal waveforms based on the image signal data and the biological signal data; and
    synchronizing the image and the biological signal waveforms to be displayed, based on the first count appended to the image signal data and the second count appended to the biological signal data.

* * * * *